US008309112B2

(12) United States Patent
Glauser et al.

(10) Patent No.: US 8,309,112 B2
(45) Date of Patent: Nov. 13, 2012

(54) COATINGS FOR IMPLANTABLE MEDICAL DEVICES COMPRISING HYDROPHILIC SUBSTANCES AND METHODS FOR FABRICATING THE SAME

(75) Inventors: Thierry Glauser, Redwood City, CA (US); Connie S. Kwok, Santa Clara, CA (US); Charles D. Claude, Sunnyvale, CA (US); Eugene T. Michal, San Francisco, CA (US); Yiwen Tang, San Jose, CA (US); Irina Astafieva, Palo Alto, CA (US); John Whatley, San Francisco, CA (US); Stephen D. Pacetti, San Jose, CA (US); Ashok Shah, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1772 days.

(21) Appl. No.: 10/746,483

(22) Filed: Dec. 24, 2003

(65) Prior Publication Data

US 2005/0147647 A1    Jul. 7, 2005

(51) Int. Cl.
*A61K 13/00* (2006.01)
(52) U.S. Cl. ...................................... 424/422
(58) Field of Classification Search .................. None
See application file for complete search history.

(56) References Cited

U.S. PATENT DOCUMENTS

| | | | | |
|---|---|---|---|---|
| 3,886,125 A * | 5/1975 | Chromecek | | 526/240 |
| 4,329,383 A | 5/1982 | Joh | | 428/36 |
| 4,733,665 A | 3/1988 | Palmaz | | 128/343 |
| 4,800,882 A | 1/1989 | Gianturco | | 128/343 |
| 4,882,168 A | 11/1989 | Casey et al. | | 424/468 |
| 4,886,062 A | 12/1989 | Wiktor | | 128/343 |
| 4,941,870 A | 7/1990 | Okada et al. | | 600/36 |
| 4,977,901 A | 12/1990 | Ofstead | | 128/772 |
| 5,112,457 A | 5/1992 | Marchant | | 204/165 |
| 5,165,919 A | 11/1992 | Sasaki et al. | | 424/488 |
| 5,272,012 A | 12/1993 | Opolski | | 428/423.1 |
| 5,292,516 A | 3/1994 | Viegas et al. | | 424/423 |
| 5,298,260 A | 3/1994 | Viegas et al. | | 424/486 |
| 5,300,295 A | 4/1994 | Viegas et al. | | 424/427 |
| 5,306,501 A | 4/1994 | Viegas et al. | | 424/423 |
| 5,328,471 A | 7/1994 | Slepian | | 604/101 |
| 5,330,768 A | 7/1994 | Park et al. | | 424/501 |
| 5,380,299 A | 1/1995 | Fearnot et al. | | 604/265 |
| 5,417,981 A | 5/1995 | Endo et al. | | 424/486 |

(Continued)

FOREIGN PATENT DOCUMENTS

EP    0 301 856    2/1989

(Continued)

OTHER PUBLICATIONS

Anonymous, *Cardiologists Draw—Up The Dream Stent*, Clinica 710:15 (Jun. 17, 1996), http://www.dialoqweb.com/cgi/document?req=1061848202959, printed Aug. 25, 2003 (2 pages).

(Continued)

*Primary Examiner* — Paul Dickinson
(74) *Attorney, Agent, or Firm* — Squire Sanders (US) LLP

(57) ABSTRACT

A segmented polyurethane and an amphiphilic random or block copolymer are disclosed. The segmented polyurethane and the amphiphilic random or block copolymer can be used for fabricating a coating for an implantable medical device such as a stent.

12 Claims, 6 Drawing Sheets

U.S. PATENT DOCUMENTS

| | | | |
|---|---|---|---|
| 5,447,724 A | 9/1995 | Helmus et al. | 424/426 |
| 5,455,040 A | 10/1995 | Marchant | 424/426 |
| 5,462,990 A | 10/1995 | Hubbell et al. | 525/54.1 |
| 5,464,650 A * | 11/1995 | Berg et al. | 427/2.3 |
| 5,569,463 A | 10/1996 | Helmus et al. | 424/426 |
| 5,578,073 A | 11/1996 | Haimovich et al. | 623/1 |
| 5,605,696 A | 2/1997 | Eury et al. | 424/423 |
| 5,609,629 A | 3/1997 | Fearnot et al. | 623/1 |
| 5,624,411 A * | 4/1997 | Tuch | 604/265 |
| 5,628,730 A | 5/1997 | Shapland et al. | 604/21 |
| 5,649,977 A | 7/1997 | Campbell | 623/1 |
| 5,658,995 A | 8/1997 | Kohn et al. | 525/432 |
| 5,667,767 A | 9/1997 | Greff et al. | 424/9.411 |
| 5,670,558 A | 9/1997 | Onishi et al. | 523/112 |
| 5,679,400 A | 10/1997 | Tuch | 427/2.14 |
| 5,700,286 A | 12/1997 | Tartaglia et al. | 623/1 |
| 5,702,754 A | 12/1997 | Zhong | 427/2.12 |
| 5,716,981 A | 2/1998 | Hunter et al. | 514/449 |
| 5,735,897 A | 4/1998 | Buirge | 623/12 |
| 5,746,998 A | 5/1998 | Torchilin et al. | 424/9.4 |
| 5,776,184 A | 7/1998 | Tuch | 623/1 |
| 5,788,979 A | 8/1998 | Alt et al. | 424/426 |
| 5,800,392 A | 9/1998 | Racchini | 604/96 |
| 5,820,917 A | 10/1998 | Tuch | 427/2.1 |
| 5,824,048 A | 10/1998 | Tuch | 623/1 |
| 5,824,049 A | 10/1998 | Ragheb et al. | 623/1 |
| 5,830,178 A | 11/1998 | Jones et al. | 604/49 |
| 5,837,008 A | 11/1998 | Berg et al. | 623/1 |
| 5,837,313 A | 11/1998 | Ding et al. | 427/2.21 |
| 5,843,156 A * | 12/1998 | Slepian et al. | 128/898 |
| 5,851,508 A | 12/1998 | Greff et al. | 424/9.411 |
| 5,858,746 A | 1/1999 | Hubbell et al. | 435/177 |
| 5,865,814 A | 2/1999 | Tuch | 604/265 |
| 5,869,127 A | 2/1999 | Zhong | 427/2.12 |
| 5,873,904 A | 2/1999 | Ragheb et al. | 623/1 |
| 5,876,433 A | 3/1999 | Lunn | 623/1 |
| 5,877,224 A | 3/1999 | Brocchini et al. | 514/772.2 |
| 5,925,720 A | 7/1999 | Kataoka et al. | 525/523 |
| 5,955,509 A | 9/1999 | Webber et al. | 514/772.7 |
| 5,971,954 A | 10/1999 | Conway et al. | 604/96 |
| 5,980,928 A | 11/1999 | Terry | 424/427 |
| 5,980,972 A | 11/1999 | Ding | 427/2.24 |
| 5,997,517 A | 12/1999 | Whitbourne | 604/265 |
| 6,010,530 A | 1/2000 | Goicoechea | 623/1 |
| 6,015,541 A | 1/2000 | Greff et al. | 424/1.25 |
| 6,033,582 A | 3/2000 | Lee et al. | 216/37 |
| 6,042,875 A | 3/2000 | Ding et al. | 427/2.24 |
| 6,051,576 A | 4/2000 | Ashton et al. | 514/255 |
| 6,051,648 A | 4/2000 | Rhee et al. | 525/54.1 |
| 6,056,993 A | 5/2000 | Leidner et al. | 427/2.25 |
| 6,060,451 A | 5/2000 | DiMaio et al. | 514/13 |
| 6,060,518 A | 5/2000 | Kabanov et al. | 514/781 |
| 6,080,488 A | 6/2000 | Hostettler et al. | 428/423.3 |
| 6,096,070 A | 8/2000 | Ragheb et al. | 623/1 |
| 6,099,562 A | 8/2000 | Ding et al. | 623/1.46 |
| 6,110,188 A | 8/2000 | Narciso, Jr. | 606/153 |
| 6,110,483 A | 8/2000 | Whitbourne et al. | 424/423 |
| 6,113,629 A | 9/2000 | Ken | 623/1.1 |
| 6,120,536 A | 9/2000 | Ding et al. | 623/1.43 |
| 6,120,904 A | 9/2000 | Hostettler et al. | 428/423.3 |
| 6,121,027 A | 9/2000 | Clapper et al. | 435/180 |
| 6,129,761 A | 10/2000 | Hubbell | 623/11 |
| 6,153,252 A | 11/2000 | Hossainy et al. | 427/2.3 |
| 6,165,212 A | 12/2000 | Dereume et al. | 623/1.13 |
| 6,203,551 B1 | 3/2001 | Wu | 606/108 |
| 6,231,600 B1 | 5/2001 | Zhong | 623/1.42 |
| 6,240,616 B1 | 6/2001 | Yan | 29/527.2 |
| 6,245,753 B1 | 6/2001 | Byun et al. | 514/56 |
| 6,251,136 B1 | 6/2001 | Guruwaiya et al. | 623/1.46 |
| 6,254,632 B1 | 7/2001 | Wu et al. | 623/1.15 |
| 6,258,121 B1 | 7/2001 | Yang et al. | 623/1.46 |
| 6,283,947 B1 | 9/2001 | Mirzaee | 604/264 |
| 6,283,949 B1 | 9/2001 | Roorda | 604/288.02 |
| 6,284,305 B1 | 9/2001 | Ding et al. | 427/2.28 |
| 6,287,628 B1 | 9/2001 | Hossainy et al. | 427/2.3 |
| 6,299,604 B1 | 10/2001 | Ragheb et al. | 604/265 |
| 6,306,166 B1 * | 10/2001 | Barry et al. | 623/1.46 |
| 6,306,176 B1 | 10/2001 | Whitbourne | 623/23.59 |
| 6,331,313 B1 | 12/2001 | Wong et al. | 424/427 |
| 6,335,029 B1 | 1/2002 | Kamath et al. | 424/423 |
| 6,346,110 B2 | 2/2002 | Wu | 606/108 |
| 6,358,556 B1 | 3/2002 | Ding et al. | 427/2.24 |
| 6,379,381 B1 | 4/2002 | Hossainy et al. | 623/1.42 |
| 6,383,500 B1 * | 5/2002 | Wooley et al. | 424/401 |
| 6,395,326 B1 | 5/2002 | Castro et al. | 427/2.24 |
| 6,419,692 B1 | 7/2002 | Yang et al. | 623/1.15 |
| 6,451,373 B1 | 9/2002 | Hossainy et al. | 427/2.25 |
| 6,494,862 B1 | 12/2002 | Ray et al. | 604/96.01 |
| 6,503,556 B2 | 1/2003 | Harish et al. | 427/2.24 |
| 6,503,954 B1 | 1/2003 | Bhat et al. | 514/772.2 |
| 6,506,437 B1 | 1/2003 | Harish et al. | 427/2.25 |
| 6,527,801 B1 | 3/2003 | Dutta | 623/1.46 |
| 6,527,863 B1 | 3/2003 | Pacetti et al. | 118/500 |
| 6,540,776 B2 | 4/2003 | Sanders Millare et al. | 623/1.15 |
| 6,544,223 B1 | 4/2003 | Kokish | 604/103.01 |
| 6,544,543 B1 | 4/2003 | Mandrusov et al. | 424/422 |
| 6,544,582 B1 | 4/2003 | Yoe | 427/2.24 |
| 6,555,157 B1 | 4/2003 | Hossainy | 427/2.24 |
| 6,558,733 B1 | 5/2003 | Hossainy et al. | 427/2.24 |
| 6,565,659 B1 | 5/2003 | Pacetti et al. | 118/500 |
| 6,572,644 B1 | 6/2003 | Moein | 623/1.11 |
| 6,585,765 B1 | 7/2003 | Hossainy et al. | 623/1.45 |
| 6,585,926 B1 | 7/2003 | Mirzaee | 264/400 |
| 7,094,256 B1 * | 8/2006 | Shah et al. | 623/1.46 |
| 7,247,313 B2 * | 7/2007 | Roorda et al. | 424/423 |
| 2001/0018469 A1 | 8/2001 | Chen et al. | 523/121 |
| 2001/0037145 A1 | 11/2001 | Guruwaiya et al. | 623/1.15 |
| 2002/0013437 A1 * | 1/2002 | McKee et al. | 526/220 |
| 2002/0077693 A1 | 6/2002 | Barclay et al. | 623/1.13 |
| 2002/0091433 A1 | 7/2002 | Ding et al. | 623/1.2 |
| 2002/0155212 A1 | 10/2002 | Hossainy | 427/2.25 |
| 2003/0040790 A1 * | 2/2003 | Furst | 623/1.11 |
| 2003/0065377 A1 | 4/2003 | Davila et al. | 623/1.13 |
| 2003/0099712 A1 | 5/2003 | Jayaraman | 424/486 |
| 2006/0078493 A1 * | 4/2006 | von Oepen | 424/1.11 |

FOREIGN PATENT DOCUMENTS

| | | |
|---|---|---|
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0 953 320 | 11/1999 |
| EP | 0 970 711 | 1/2000 |
| EP | 0 982 041 | 3/2000 |
| EP | 1 273 314 | 1/2003 |
| JP | 2001-190687 | 7/2001 |
| WO | WO 8906957 A * | 8/1989 |
| WO | WO 91/12846 | 9/1991 |
| WO | WO 95/10989 | 4/1995 |
| WO | WO 96/40174 | 12/1996 |
| WO | WO 97/10011 | 3/1997 |
| WO | WO 97/45105 | 12/1997 |
| WO | WO 97/46590 | 12/1997 |
| WO | WO 98/17331 | 4/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 11/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/74414 | 10/2001 |
| WO | WO 02/03890 | 1/2002 |

| WO | WO 02/26162 | 4/2002 |
| WO | WO 02/34311 | 5/2002 |
| WO | WO 02/056790 | 7/2002 |
| WO | WO 02055122 A1 * | 7/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |

OTHER PUBLICATIONS

Anonymous, *Heparin-coated stents cut complications by 30%*, Clinica 732:17 (Nov. 18, 1996), http://www.dialog.web.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?req=1061848017752, printed Aug. 25, 2003 (2 pages).

Aoyagi et al., *Preparation of cross-linked aliphatic polyester and application to thermo-responsive material*, Journal of Controlled Release 32:87-96(1994).

Barath et al., *Low Dose of Antitumor Agents Prevents Smooth Muscle Cell Proliferation After Endothelial Injury*, JACC 13(2): 252A (Abstract) (Feb. 1989).

Barbucci et al., *Coating of commercially available materials with a new heparinizable material*, J. Biomed. Mater. Res. 25:1259-1274 (Oct. 1991).

Chung et al., *Inner core segment design for drug delivery control of thermo-responsive polymeric micelles*, Journal of Controlled Release 65:93-103 (2000).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5)1347-1353 (Nov. 1989).

Eigler et al, *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).

Liu et al., *Drug release characteristics of unimolecular polymeric micelles*, Journal of Controlled Release 68:167-174 (2000).

Marconi et al., *Covalent bonding of heparin to a vinyl copolymer for biomedical applications*, Biomaterials 18(12):885-890 (1997).

Matsumaru et al., *Embolic Materials for Endovascular Treatment of Cerebral Lesions*, J. Biomater. Sci. Polymer Edn 8(7):555-569 (1997).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

Nordrehaug et al., *A novel biocompatible coating applied to coronary stents*, European Heart Journal 14, p. 321 (P1694), Abstr. Suppl. (1993).

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).

Peng et al., *Role of polymers in improving the results of stenting in coronary arteries*, Biomaterials 17:685-694 (1996).

Shigeno, *Prevention of Cerebrovascular Spasm by Bosentan, Novel Endothelin Receptor*, Chemical Abstract 125:212307 (1996).

van Beusekom et al., *Coronary stent coatings*, Coronary Artery Disease 5(7):590-596 (Jul. 1994).

Wilensky et al., *Methods and Devices for Local Drug Delivery in Coronary and Peripheral Arteries*, Trends Cardiovasc. Med. 3(5):163-170 (1993).

Yokoyama et al., *Characterization of physical entrapment and chemical conjugation of adriamycin in polymeric micelles and their design for in vivo delivery to a solid tumor*, Journal of Controlled Release 50:79-92 (1998).

* cited by examiner

COATINGS FOR IMPLANTABLE MEDICAL DEVICES COMPRISING HYDROPHILIC SUBSTANCES AND METHODS FOR FABRICATING THE SAME

BACKGROUND

1. Field of the Invention

This invention is directed to coatings for implantable medical devices, such as drug eluting vascular stents.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer. Once the stent has been implanted at the treatment site, the therapeutic substance has a sustained release profile from the polymer.

Although local administration of therapeutic agents via stents has shown favorable results in reducing restenosis, improvements can be made to stent coatings. The controlled release of hydrophilic drugs, peptides, proteins, oligonucleotides, plasmids and DNA can be difficult with polymeric coatings due to the osmotic pressure from water absorption generated by the hydrophilicity of the agent. Upon penetration of water into the coating, the permeability of the coating for the hydrophilic drug is significantly increased, resulting in the elution of the drug at a therapeutically ineffective rate. Accordingly, it is desirable to provide a coating that includes a hydrophobic fraction to minimize water absorption. Moreover, hydrophobic polymers tend to adhere better to stent substrates and the mechanical integrity of high molecular weight hydrophobic polymers is typically superior. If the matrix is too hydrophobic, however, the polymer may have a poor solubility in solvent systems which are required to dissolve the drug to form a homogenous coating solution. The hydrophilic drug will rapidly phase separate in an uncontrolled manner resulting in drug aggregation. Drug aggregation produces unpredictable and variable release rate profiles. The result is a drug coating on a stent that is irreproducible such that each coated stent will have variable drug content and distribution with different release profiles. Particles of hydrophilic drugs also weaken a hydrophobic coating and cause local areas of high swelling. As a manufacturing stand point, replication of the same coating with similar drug distribution and release rate profile is desired.

A hydrophilic fraction in a coating is needed to make the agent more compatible in the coating, decrease the size of the drug aggregation, and minimize variability of the release rate of the drug from the coating. Hydrophilicity is important for both solution stability and the equal distribution of the drug in the coating. If, however, the coating is highly hydrophilic, the stent coating will rapidly absorb water. The rapid absorption of water plasticizes the polymer, resulting in a depression of the glass transition temperature to produce a soft gel-like coating. The mechanical properties of a plasticized gel-like reservoir are insufficient for wet expansion. The polymer can tear upon expansion and produce a coating with undesirable defects. Excessive water swelling not only weakens the polymer, but also increases the diffusivity of the drug, resulting in loss of release control.

The embodiments of the present invention address these concerns as well as others that are apparent by one having ordinary skill in the art.

SUMMARY

Figure 1A:
FIGS. 1A-1F, 4, and 5 are microphotographs of stents coated according to embodiments of the present invention after simulated in vitro testing.
Figure 1B:
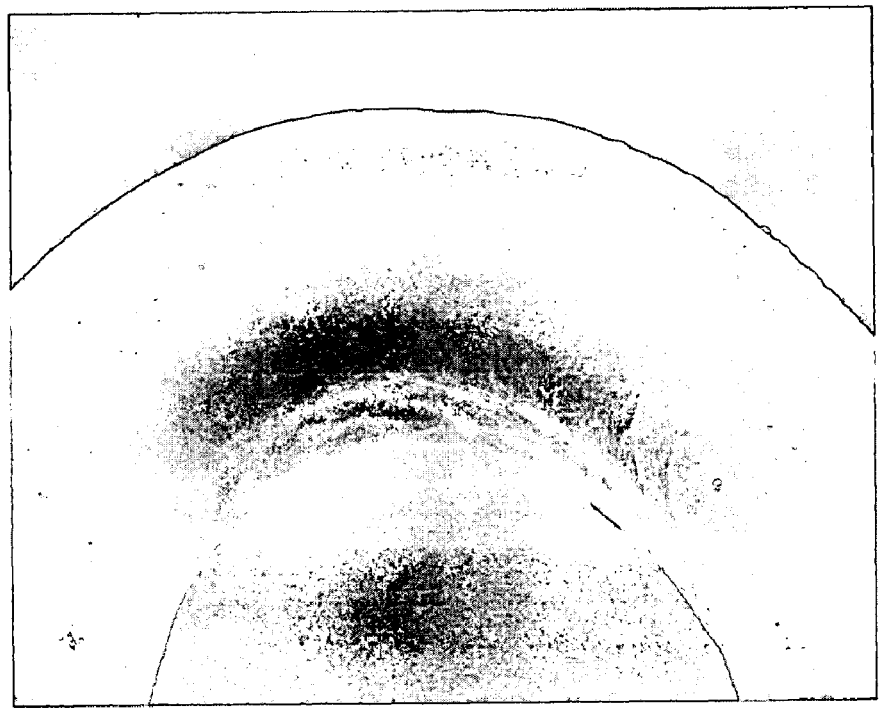
Figure 1C:
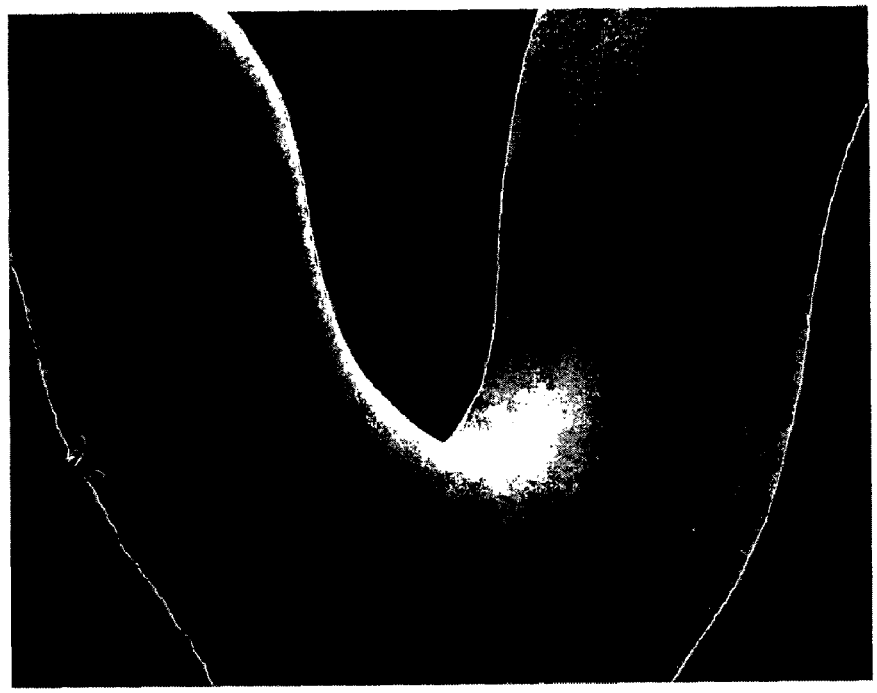
Figure 1D:
Figure 1E:
Figure 1F:
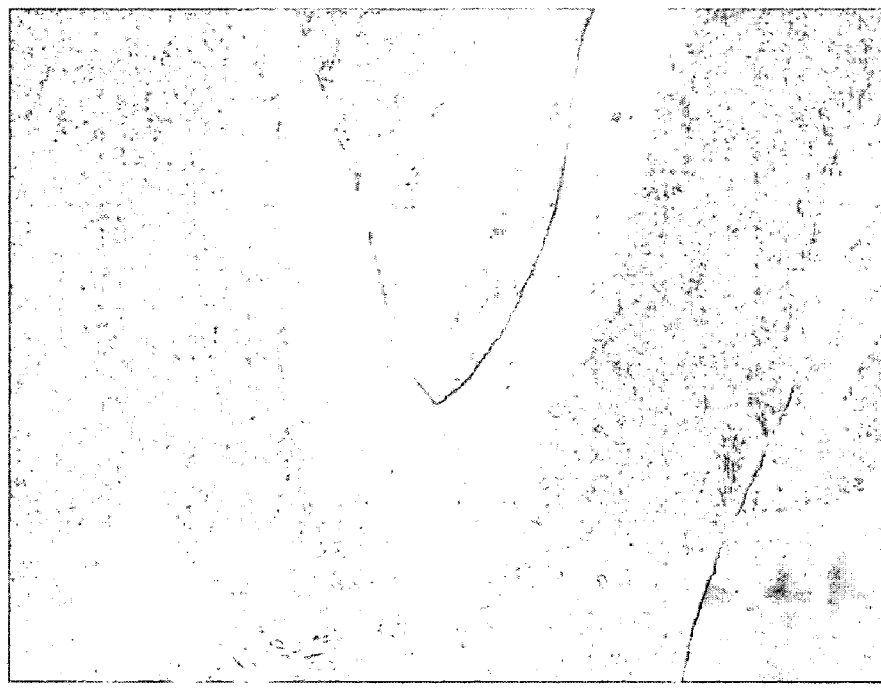

A medical article is provided, the medical article comprises an implantable substrate and a polymer coating disposed at least on a portion of the substrate, the coating including a segmented polyurethane comprising a soft segment and a hard segment. Examples of segmented polyurethanes that can be used include poly(urethane-urea), poly(ether urethane) and poly(carbonate urethane).

A medical article is provided, the medical article comprises an implantable substrate and a polymer coating disposed at least on a portion of the substrate, the coating including an amphiphilic copolymer comprising at least one hydrophobic moiety and at least one hydrophilic moiety. Examples of amphiphilic polymers that can be used include acrylic copolymers, such as a random copolymer or a block copolymer, for example an ABA block copolymer and an AB block-copolymer. The amphiphilic block-copolymer can be a product of living free radical copolymerization of plurality of monomers with initiation-transfer agent termination of the living macro-chains.

The coating can further include a hydrophilic therapeutic agent, such as a water soluble drug, for example cyclic-RGD peptide, poly(L-arginine), poly(D-arginine), poly(D,L-arginine), poly(L-lysine), poly(D-lysine), poly(δ-guanidino-α-aminobutyric acid), a racemic mixture of poly(L-arginine) with poly(D-arginine), elastin mimetic polypeptides, and blends thereof.

DETAILED DESCRIPTION

1. Terms and Definitions

The term "random copolymer" is defined in accordance with terminology used by the International Union of Pure and Applied Chemistry (IUPAC). The IUPAC defines a random copolymer as a copolymer consisting of macromolecules in which the probability of finding a given monomeric unit at any given site in the chain is independent of the nature of the adjacent units. In a random copolymer, the sequence distribution of monomeric units follows Bernoullian statistics.

The term "block-copolymer" is also defined in accordance with the terminology used by the International Union for Pure and Applied Chemistry (IUPAC). "Block-copolymer" refers to a copolymer containing a linear arrangement of blocks. The block is defined as a portion of a polymer molecule in which the monomeric units have at least one constitutional or configurational feature absent from the adjacent portions.

The term "AB block-copolymer" is defined as a block-copolymer having moieties A and B arranged according to the general formula -$\{[A-]_m-[B]_n\}-_x$, where each of "m," "n," and "x" is a positive integer, and $m \geq 2$, and $n \geq 2$.

The term "ABA block-copolymer" is defined as a block-copolymer having moieties A and B arranged according to the general formula -$\{[A-]_m-[B-]_n-[A]_p\}-_x$, where each of "m," "n," "p," and "x" is a positive integer, and $m \geq 2$, and $n \geq 2$, and $p \geq 2$.

The term "ABC block-copolymer" is defined as a block-copolymer having moieties A, B, and C arranged according to the general formula -$\{[A-]_m-[B-]_n-[C]_p\}_x-$, where each of "m," "n," "p," and "x" is a positive integer, and $m \geq 2$, and $n \geq 2$, and $p \geq 2$.

The blocks of the block-copolymers need not be linked on the ends, since the values of the integers determining the number of blocks are such as to ensure that the individual blocks are usually long enough to be considered polymers in their own right. Accordingly, the ABA block copolymer can be named poly A-block-co-poly B block-co-poly A block-copolymer, the ABC block copolymer can be named poly A-block-co-poly B block-co-poly C block-copolymer and the AB block copolymer can be named poly A-block-co-poly B block-copolymer. Blocks "A," "B," and "C," typically, larger than three-block size, can be alternating or random.

The term "segmented polyurethanes" is defined as polyurethanes having a soft segment and a hard segment.

The term "moiety" is defined as a portion of a complete structure of a copolymer, the portion to include at least 2 atoms joined together in a particular way. The term "moiety" includes functional groups and/or discreet bonded residues that are present in the macromolecule of a copolymer. The term "moiety" as used herein is inclusive of individual units in the random copolymers. The term "moiety" as used herein is also inclusive of entire polymeric blocks in the block-copolymers.

The term "poly(urethane-urea)" is defined as a polymer having both the urethane moiety (—NH—C(O)—O—) and the urea moiety (—NH—C(O)—NH—).

The term "acrylic copolymers" is defined as copolymers having at least one unit derived from either acrylic acid $CH_2$=CH—COOH or from methacrylic acid $CH_2$=C($CH_3$)—COOH.

A polymer is classified as "hydrophilic" or "hydrophobic" depending on the value of the polymer's Hildebrand solubility parameter. The term "Hildebrand solubility parameter" is defined as a parameter δ indicating the cohesive energy density of a substance. The δ parameter is determined as follows:

$$\delta = (\Delta E/V)^{1/2}$$

where δ is the solubility parameter, $(cal/cm^3)^{1/2}$; $\Delta E$ is the energy of vaporization, cal/mole; and V is the molar volume, $cm^3$/mole.

The terms "hydrophilic moiety" and "hydrophobic moiety" is each defined as a moiety capable of forming a hydrophilic or a hydrophobic homopolymer, respectively. In other words, if a homopolymer containing exclusively a hydrophilic moiety were synthesized, the homopolymer would be hydrophilic; if a homopolymer containing exclusively a hydrophobic moiety were synthesized, the homopolymer would be hydrophobic.

The term "amphiphilic copolymers" is defined as copolymers the structure of which includes both hydrophilic and hydrophobic moieties.

The term "water soluble drug" is defined as a drug which can form a stable, clear aqueous solution containing, at equilibrium, not less than about 5 mass % of the drug. The drug is defined as a "small-molecule drug" if the molecular of the active agent in the drug is less than about 10,000 Daltons.

2. Embodiments of the Invention

A coating for an implantable medical device, such as a stent, according to embodiments of the present invention, can include any one or all of the following three layers:

(a) a primer layer;

(b) a drug-polymer layer (also referred to as "reservoir" or "reservoir layer") or alternatively a polymer free drug layer; and/or (c) a topcoat layer.

Each layer of the stent coating can be formed on the stent by dissolving the polymer or a blend of polymers in a solvent, or a mixture of solvents, and applying the resulting polymer solution on the stent by spraying or immersing the stent in the solution. After the solution has been applied onto the stent, the coating is dried by allowing the solvent to evaporate. The process of drying can be accelerated if the drying is conducted at an elevated temperature.

To incorporate a drug into the reservoir layer, the drug can be combined with the polymer solution that is applied onto the stent as described above. Alternatively, to fabricate a polymer free drug layer, the drug can be dissolved in a suitable solvent or mixture of solvents, and the resulting drug solution can be applied on the stent by spraying or immersing the stent in the drug solution.

Instead of introducing the drug as a solution, the drug can be introduced as a colloidal system, such as a suspension in an appropriate solvent phase. To make the suspension, the drug can be dispersed in the solvent phase using conventional techniques used in colloid chemistry. Depending on a variety of factors, e.g., the nature of the drug, those having ordinary skill in the art can select the solvent to form the solvent phase of the suspension, as well as the quantity of the drug to be dispersed in the solvent phase. The suspension can be mixed with a polymer solution and the mixture can be applied on the stent as described above. Alternatively, the drug suspension can be applied on the stent without being mixed with the polymer solution.

The drug-polymer layer can be applied directly onto at least a part of the stent surface to serve as a reservoir for at least one active agent or a drug which is incorporated into the reservoir layer. The optional primer layer, free of any drugs, can be applied between the stent and the reservoir to improve the adhesion of the reservoir to the stent. The topcoat layer can be applied over at least a portion of the reservoir layer to serve as a rate limiting membrane. The topcoat layer can be essentially free from any active agents or drugs.

According to embodiments of the present invention, the drug-polymer layer can contain a water-soluble, small molecule drug, or a blend of more than one of such drugs. The mass ratio between the drug and the polymer in the drug polymer layer can be between about 1:10 and about 1:3, such as between about 1:9 and about 1:4, for example, about 1:6.

A. Drugs

Water-soluble, small molecule drugs that can be incorporated in the drug-polymer layer include proteins, peptides, biologically active compounds conjugated to peptides, anti-inflammatory, anti-proliferative, or antimicrobial drugs. In one embodiment, the drugs include cyclic-RGD (c-RGD) peptide, poly(L-arginine), poly(D-arginine), poly(D,L-arginine), poly(L-lysine), poly(D-lysine), poly(δ-guanidino-α-aminobutyric acid), a racemic mixture of poly(L-arginine), poly(D-arginine), and elastin mimetic polypeptides. The term "cyclic RGD" refers to a peptide that is a product of condensation of arginine (amino acid R), glycine (aminoacetic acid or amino acid G), and aspartic acid (amino acid D), the peptide having a cyclic structure.

The terms "poly(L-arginine)," "poly(D-arginine)," "poly (D,L-arginine)" are intended to include L-, D-, and/or D, L-arginine in both its polymeric and oligomeric form. Polymers and/or oligomers of L-, D-, and/or D, L-arginine that can be used comprise a plurality of repeating monomeric amino acid units connected with peptide bonds, each unit including 1-guanidinopropyl radical having the structure —CH$_2$—CH$_2$—CH$_2$—NH—C(NH$_2$)=NH. In one embodiment, a heptamer (R7) (p=7), or a nonamer (R9) (p=9) of L-arginine, can be used.

Elastin mimetic polypeptides are protein pentamers comprising a number of amino acids and having the formula

where V is valine (2-amino-3-methylbutyric acid), I is isoleucine (2-amino-3-methylvaleric acid), P is proline [(S)-2-pyrrolidine carboxylic acid], G is glycine (aminoacetic acid), and Xaa is an amino acid which is valine in the first four repeating units and either isoleucine or lysine [(S)-2,6-diaminohexanoic acid or K] in the fifth repeating unit. The abbreviation "V/I" signifies that either valine or isoleucine, but not both, can be present.

B. Polymers

The stent coating, in which a water-soluble, small molecule drug described above is incorporated, includes at least one polymer. The polymer(s) that can be used include (1) segmented polyurethanes, e.g., segmented poly(urethane ureas), or (2) acrylic copolymers, as discussed below.

1. Segmented Polyurethanes

According to embodiments of present invention, the soft segment of segmented polyurethanes that can be used for making the stent coatings can be derived from a polyol and the hard segment can be derived from an isocyanate. The soft segment provides the polyurethane with the properties of an elastomer. Thus, the soft segment can serve to prevent or at least reduce the cracking of the coating. The hard segment provides the stent coating with mechanical strength. In addition, segmented polyurethanes that can be used possess a high degree of hydrogen bonding to provide good adhesion of the stent coating to the stent.

Various types of segmented polyurethanes that can be used for making the stent coatings include poly(urethane ureas). Formula (II) demonstrates a basic structure of an exemplary class of segmented poly(urethane ureas) based on an aromatic diisocyanate.

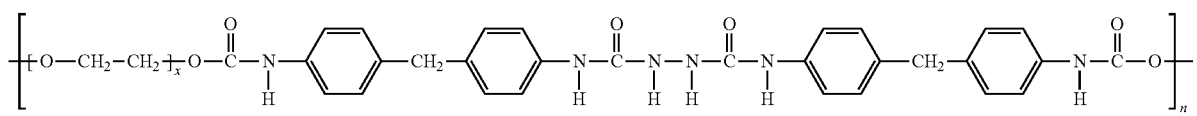

(II)

As can be seen from formula (II), the hard segment includes both the urethane moiety (—NH—C(O)—O—) and the urea moiety (—NH—C(O)—NH—); the soft segment is derived from a low molecular weight poly(ethylene glycol) (x is about 40).

One example of a segmented poly(urethane urea) that can be used includes BIOSPAN polymers available from Polymer Technology Group of Berkeley, Calif. BIOSPAN is a trade name of a group of polyurethane elastomers based on an aromatic poly(ether urethane urea) with a soft segment derived from poly(tetramethylene oxide) and a hard segment derived from diphenylmethane diisocyanate. To fabricate a BIOSPAN polymer, mixed diamines can further be used as chain extenders.

In addition to, or instead of, the BIOSPAN polymers, alternative segmented poly(urethane ureas) can be used. In the alternative poly(urethane ureas), a hard segment is derived from a diisocyanate, a soft segment is derived from a polyol, and diamines are used as chain extenders. Examples of diisocyanates that can be used include aromatic isocyanates (e.g., 2,4-toluene diisocyanate), cycloaliphatic isocyanates (e.g., 1,4-cyclohexane diisocyanate, methylene dicyclohexyl diisocyanate, or 1,6-hexamethylene diisocyanate), and aliphatic diisocyanates (e.g., 1,6-diisocyanato hexane or 1,6-diisocyanato dodecane).

Examples of polyols that can be used include poly(ethylene glycol), poly(propylene glycol), poly(tetramethylene glycol), poly(ethylene glycol-co-propylene glycol), and PLURONIC products. PLURONIC is a trade name of a group of surfactants based on poly(ethylene oxide-co-propylene oxide). PLURONIC products are available from BASF Corp. of Parsippany, N.J. Examples of chain-extending diamines include 1,4-butanediamine, 1,5-pentanediamine, 1,3-diaminocyclohexane, 1,4-diaminocycloxexane, and mixtures thereof.

In addition to, or instead of, poly(urethane ureas), alternatively, other types of segmented polyurethanes can be used to fabricate stent coatings. Examples of the alternative segmented polyurethanes that can be used include poly(ether urethanes) and poly(carbonate urethanes). If poly(ether urethanes) are used in the drug-polymer layer of the stent coating, it may be necessary to use a primer layer to improve adhesion of the stent coating to the stent. Examples of particular kinds of poly(ether urethanes) that can be utilized include PELLETHANE and TECOFLEX. PELLETHANE is a trade name of a family of thermoplastic polyurethane elastomers available from Dow Chemical Co. of Midland, Mich. TECOFLEX is a trade name of a family of thermoplastic polyurethane elastomers available from Thermedics Polymer Products Co. of Wilmington, Mass.

In addition to a segmented polyurethane and a drug, a drug-polymer layer of a stent coating can optionally include some stabilizing additives such as poly(methacrylates), and/or antioxidants such as vitamin E. Also, in order to increase the rate of release of a drug from the stent coating, pore forming agents can be blended with a segmented polyurethane in the drug-polymer layer. Examples of pore forming agents that can be used include low molecular weight poly(ethylene glycol) (e.g., having molecular weight of about 3,400 Daltons), poly(N-vinyl pyrrolidone), sugars, and inorganic salts (e.g., sodium phosphate).

2. Acrylic Copolymers

According to embodiments of the present invention, acrylic copolymers can be used for making the stent coatings include both random copolymers and block-copolymers. The acrylic copolymers that can be used can be amphiphilic copolymers and can include at least one hydrophobic moiety and at least one hydrophilic moiety. For example, in case of random copolymers, some constituent units of the copolymers can include a hydrophobic moiety while other constituent units can include a hydrophilic moiety. Examples of block-copolymers that can be used include AB-, ABA, and ABC block-copolymers.

In case of AB copolymers, either moiety A or moiety B can be a hydrophobic moiety, and the other moiety can be a hydrophilic moiety. In case of ABA block-copolymers, the central B-block can be hydrophobic, and the terminal A blocks can be hydrophilic, or vice versa. In case of ABC block copolymers, either moiety A, B, or C, or any two of A, B, and C can be a hydrophobic moiety or moieties, while the remaining moiety or moieties can be a hydrophilic moiety or moieties, or vice versa.

Whichever moiety in the amphiphilic copolymer has lower Hildebrand $\delta$ value compared to the $\delta$ value of the other moiety in the copolymer is designated as a hydrophobic moiety, and the moiety with higher $\delta$ value is designated as a hydrophilic moiety. If more than two moieties are used in the copolymer, then each can be ranked in order of its $\delta$ value. For the practice of the present invention, the value of $\delta$ of a particular moiety is inconsequential for classifying a moiety as hydrophobic or hydrophilic. In one embodiment, the $\delta$ value defining the boundary between the hydrophobic and hydrophilic moieties of the copolymer can be about 10 (cal/cm$^3$)$^{1/2}$. According to this exemplary embodiment, the hydrophobic moieties of the copolymer can have the $\delta$ value below 10 (cal/cm$^3$)$^{1/2}$, and the hydrophilic moieties can have the $\delta$ value of about 10 (cal/cm$^3$)$^{1/2}$ or higher.

If random copolymers comprising moieties A and B are used, in the macromolecules of the random AB copolymer moieties A and B are distributed along the chains randomly. The random acrylic copolymers can be obtained by common synthetic methods, for example, by radical copolymerization of acrylic monomers in bulk, solution, suspension, or emulsion, in the presence of suitable initiators. Examples of standard initiators of radical polymerization can be used include 2,2-dimethoxy-2-phenol acetophenone. Benzophenone can be optionally added to 2,2-dimethoxy-2-phenol acetophenone as a photosensitizer.

If the block-copolymers are used, moieties A, B, and C can be arranged as A, B and C polymeric blocks, as illustrated by formula (III):

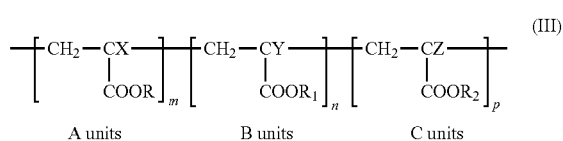

wherein:
(a) m, n, p are all integers, wherein m>0, n>0, and p≧0;
(b) X, Y, and Z is each, independently, hydrogen or an alkyl group, for example, methyl group; and
(c) R, R$_1$, and R$_2$ is each, independently, a straight-chained or branched substituted or unsubstituted alkyl group, or substituted or unsubstituted aryl group, where the substitutents in the aryl group include halogens, hydroxyl, carboxyl or amino groups.

The polymer represented by formula (III) can be an AB block-copolymer, an ABA block-copolymer, or an ABC block-copolymer. For example, if p=0, the polymer of formula (III) is an AB block-copolymer. If p ≠0, the polymer of formula (IV) is either an ABA block-copolymer or an ABC block-copolymer. It is an ABA block-copolymer if, when p ≠ 0, both X=Z and R=R$_2$. It is an ABC block-copolymer, if, when p ≠0, either X ≠Z, or R ≠R$_2$, or both X ≠Z, and R ≠R$_2$.

The structure of a random copolymer is generally similar to the structure of formula (III), except the A-, B-, and C-units in the random copolymer are distributed randomly and not in blocks.

One synthetic method that can be used to obtain the block copolymers represented by formula (III), is the method of living free radical copolymerization with initiation-transfer agent termination of the living macro-chains (the inferter process). The inferter process utilizes an initiator capable of undergoing thermal and/or photolytic free radical decomposition. Examples of suitable initiators include benzyl-N,N-diethyldithiocarbamate (BDC) or p-xylene-N,N-diethyldithiocarbamate (XDC). BDC is a derivative of toluene and has the formula

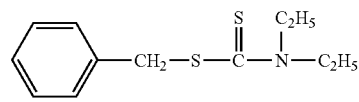

XDC is a derivative of p-xylene and has the formula

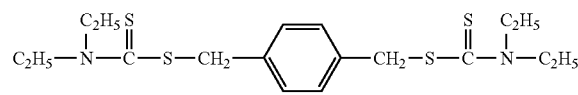

The BDC and XDC initiators can be prepared synthetically. To synthesize BDC, sodium N,N-diethyldithiocarbamate can be combined with benzyl bromide in an anhydrous methanol solution. The ratio between sodium N,N-diethyldithiocarbamate and benzyl bromide can be close to equimolar. The mixture can be stirred for about 24 hours at about room temperature to yield BDC. The process can be completed by evaporating methanol at a reduced pressure and vacuum distillation. The synthesis of XDC is similar, except instead of benzyl bromide, α,α-dibromo-p-xylene is used, and the molar ratio between sodium N,N-diethyldithiocarbamate and α,α-dibromo-p-xylene can be about 1:2.3. The product of reaction is XDC which can be purified by re-crystallization in methanol.

One possible path of the process of decomposition of an initiator is shown for BDC by scheme (IV):

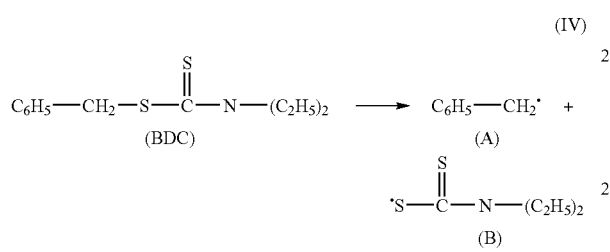

As a result of decomposition of BDC, two types of radicals are generated: the benzylic radical (species A), which undergoes free-radical addition to a monomer molecule initiating polymerization, and the dithiocarbamate radical, which terminates by heterolytic radical combination. One possible path of polymerization is shown by reaction schemes (V) and (VI) below.

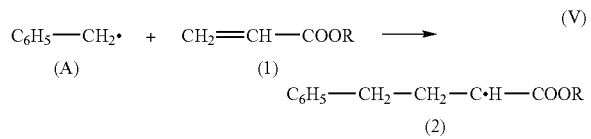

In reaction (VI), radical A serves as a free-radical initiator reacting with the monomer 1 creating reactive species (2). The reactive species (2) can further react with radical B acting as a transfer agent terminator, as shown by reaction (VI). The reactive species (3) shown by reaction (VI) below, in the presence of monomer and light will undergo heterolytic cleavage yielding the reactive polymer chain and the chain transfer agent, species B. The process is propagated until monomer (1) has been consumed:

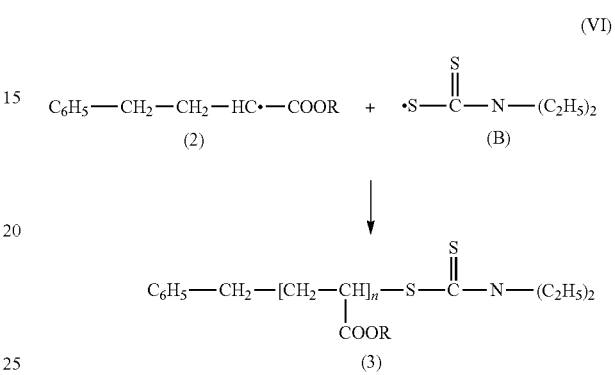

Following the completion of polymerization, monomer (1) can be added and the process analogous to the process described by reactions (V)-(VII) can be repeated, resulting in formation of an AB block copolymer. If a difunctional or multifunctional inferter is used, an ABA block-copolymer can be obtained in a similar fashion.

The hydrophobic moiety forming the random or block copolymer (B-blocks in formula IV) can be derived from unsaturated monomers, for example, unsubstituted or substituted acrylates or vinyl monomers having a general formula $CH_2=CX\text{-}M$, where X is hydrogen or methyl and M is a substituted or unsubstituted aryl group or an ester group $O=C(OR)-$, (R is an alkyl or aryl).

Some monomers that can be used to form the hydrophobic moiety are summarized in Table 1. Other monomers described by the formula $CH_2=CX\text{-}M$ can be used, if desired.

TABLE 1

| No. | Monomer, $CH_2=CX-M$ | Abbreviation | X | M |
|---|---|---|---|---|
| 1 | Methyl methacrylate | MMA | $CH_3$ | $-C(=O)OCH_3$ |
| 2 | Ethyl methacrylate | EMA | $CH_3$ | $-C(=O)O-CH_2-CH_3$ |
| 3 | n-Butyl methacrylate | BMA | $CH_3$ | $-C(=O)O-CH_2-CH_2-CH_2-CH_3$ |
| 4 | Lauryl methacrylate | LMA | $CH_3$ | $-C(=O)O-(CH_2)_{11}-CH_3$ |
| 5 | Styrene (vinyl benzene) | ST | H | $-C_6H_5$ |

The hydrophilic moiety forming the random or block copolymer can be derived from unsaturated monomers, for example, unsubstituted or substituted acrylates or vinyl monomers having a general formula $CH_2=CX-M$, where X is hydrogen or methyl and M is a substituted or unsubstituted aromatic group or an ester group $O=C(OR)-$ (R is hydrogen or a hydroxyalkyl group). Some monomers that can be used to form the hydrophilic moiety are summarized in Table 2.

TABLE 2

| No. | Monomer, $CH_2=CX-M$ | Abbreviation | X | M |
|---|---|---|---|---|
| 1 | 2-hydrohyethyl methacrylate | HEMA | $CH_3$ | $-C(=O)-O-CH_2-CH_2-OH$ |
| 2 | Acrylic acid | AA | H | $-C(=O)-OH$ |
| 3 | Methacrylic acid | MAA | $CH_3$ | $-C(=O)-OH$ |
| 4 | N-vinyl pyrrolidone | VP | H | $-N(CH_2-CH_2-C(=O)-CH_2)-$ (ring) |
| 5 | Poly(ethylene glycol)-acrylate | PEGA | H | $-C(=O)-O-[CH_2-CH_2-O]_n-H$ |

Monomers described by the formula $CH_2=CX-M$ other than those shown in Table 2 can be also used, if desired, for example, 2-methacryloylethyl phosphoryl choline, phosphoryl choline methacrylate, 2-acrylamido-2-methyl-1-propanesulfonic acid, 3-sulfopropyl acrylate, 3 sulfopropyl methacrylate, vinylsulfonic acid, 4-styrenesulfonic acid and 3-allyloxy-2-hydroxypropanesulfonic acid.

Optionally, after the acrylic random or block-copolymers have been synthesized, they can be mixed with stabilizing additives, and/or antioxidants, and/or pore forming agents described above.

The segmented polyurethanes and the acrylic random and block-copolymers described above can be used for making any layer of the stent coating. Both the segmented polyurethanes and the acrylic random and block-copolymers described above can be used alone or in combination with other suitable polymers to make the coating. In other words, the copolymer can be blended or layered with other polymers. Poly(ethylene-co-vinyl alcohol) (EVAL) is one example of a polymer than can be employed. EVAL is a product of hydrolysis of ethylene-vinyl acetate copolymers and may also be a terpolymer including up to 5 molar % of units derived from styrene, propylene and other suitable unsaturated monomers.

Representative examples of other suitable polymers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D, L-lactic acid), poly(glycolic acid-co-trimethylene carbonate), poly(glycerol-sebacate), polyphosphoester, polyphosphoester urethane; poly(amino acids), cyanoacrylates, poly (trimethylene carbonate), poly(iminocarbonate), co-poly (ether-esters) (e.g. PEO/PLA), polyalkylene oxalates, polyphosphazenes, biomolecules (such as fibrin, fibrinogen, cellulose, starch, collagen and hyaluronic acid), polyurethanes other than those described above, silicones, polyesters, polyolefins, polyisobutylene and ethylene-alphaolefin copolymers, acrylic polymers and copolymers other than those described above, vinyl halide polymers and copolymers (such as polyvinyl chloride), polyvinyl ethers (such as polyvinyl methyl ether), polyvinylidene halides (such as polyvinylidene fluoride and polyvinylidene chloride), polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, other polycarbonates, polyoxymethylenes, polyimides, polyethers, epoxy resins, other polyurethanes, rayon, rayon-triacetate, cellulose, cellulose acetate, cellulose butyrate, cellulose acetate butyrate, cellophane, cellulose nitrate, cellulose propionate, cellulose ethers, soluble fluorinated polymers and carboxymethyl cellulose.

The embodiments of the present invention are described in connection with a stent, e.g., balloon expandable or self-expandable stents; however, other implantable medical devices can also be coated with the described block copolymers. Examples of such implantable devices include stent-grafts, grafts (e.g., aortic grafts), artificial heart valves, cerebrospinal fluid shunts, pacemaker electrodes, and endocardial leads (e.g., FINELINE and ENDOTAK, available from Guidant Corp. of Santa Clara, Calif.). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum.

"MP20N" consists of 50% cobalt, 20% nickel, 20% chromium, and 10% molybdenum. Devices made from bioabsorbable or biostable polymers could also be used with the embodiments of the present invention.

Embodiments of the present invention are further illustrated by the following examples.

EXAMPLE 1

Synthesis of an ABA Block Copolymer #1
(PSPMA-PBMA-PSPMA)

As a first step, a monomer BMA was dissolved in 2-butanone (also known as methyl ethyl ketone) and an initiator XDC was added. The amounts of components are summarized in Table 3.

TABLE 3

| No. | Component | Experimental amount of the component | |
|---|---|---|---|
| | | mmol | g |
| 1 | BMA | 140.700 | 19.98 |
| 2 | 2-butanone | — | 59.41 |
| 3 | XDC | 0.287 | 0.1151 |

The solution of BMA and XDC in 2-butanone was placed into a borosilicate vial, purged with dry nitrogen for about 30 minutes and the vial was sealed. The contents of vial were subjected to UV radiation at a wavelength within a range of between about 310 nm and about 400 nm, for about 12 hours. The vial was then opened and the contents were added dropwise to ethanol cooled to a temperature of about −76° C. As a result, poly(butylmethacrylate)-XDC (PBMA-XDC) was precipitated. The precipitate was collected using a vacuum funnel and vacuum-dried.

As a second step, PBMA-XDC obtained as described above was combined with 3-sulfopropylmethacrylate (SPMA) and aqueous 2-butanone in the amounts shown in Table 4.

TABLE 4

| No. | Component | Weight fraction | Amount, grams |
|---|---|---|---|
| 1 | PBMA-XDC | 0.75 | 10.00 |
| 2 | 3-sulfopropylmethacrylate | 0.25 | 3.33 |
| 3 | 2-butanone/water | — | 40.00 |

The blend of PBMA-XDC, 3-sulfopropylmethacrylate, and 2-butanone was placed into a borosilicate vial, purged with dry nitrogen for about 10 minutes and the vial was sealed. The contents of vial were subjected to UV radiation at a wavelength within a range of between about 310 nm and about 400 nm, for about 12 hours. The vial was then opened and the contents were added dropwise to water and vigorously stirred causing precipitation of a poly(3-sulfopropyl methacrylate)-block-poly(butylmethacrylate)-block-poly(3-sulfopropylmethacrylate)-XDC. The precipitate was collected using a vacuum funnel and vacuum-dried followed by hydrolysis in the presence of potassium ethoxide to remove the N,N-diethyl-dithiocarbamate functionality. As a result of the described process, an ABA block copolymer, poly(3-sulfopropylmethacrylate)-block-poly(butylmethacrylate)-block-poly(3-sulfopropyl methacrylate), was precipitated, the ABA block copolymer having the structure (VII):

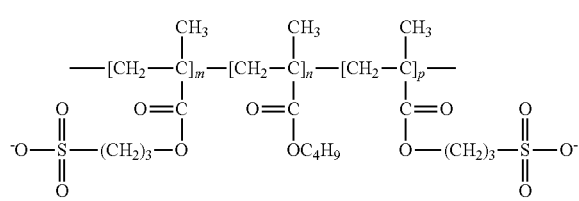

The molecular weight of the PBMA-based mid-blocks (B blocks) was about 66,700 Daltons as measured by the method of gel-permeation chromatography (GPC) corresponding to the value of n ~470, and the molecular weight of the poly(3-sulfopropylmethacrylate)-based end blocks (A blocks) was about 11,100 Daltons, corresponding to values of m ~54 and p ~54.

EXAMPLE 2

Synthesis of an ABA Block Copolymer #2
(PMAA-PBMA-PMAA)

As a first step, PBMA-XDC can be synthesized as described in Example 1. As a second step, PBMA-XDC can be combined in a vial with methacrylic acid (MAA) and 2-butanone in the amounts shown in Table 5.

TABLE 5

| No. | Component | Theoretical amount of the component | | Experimental amount of the component | |
|---|---|---|---|---|---|
| | | mmol | g | mmol | g |
| 1 | PBMA-XDC | 0.016 | 2.50 | 0.013 | 2.03 |
| 2 | 2-butanone | — | 12.40 | — | 10.19 |
| 3 | Methacrylic acid | 7.20 | 0.625 | 9.10 | 0.78425 |

The blend of PBMA-XDC, methacrylic acid and 2-butanone can be subjected to UV radiation at a wavelength within a range of between about 310 nm and about 400 mm, for about 32.5 hours. The vial can be then opened, the solvent can be removed by evaporation, the contents can be dissolved in tetrahydrofuran and the solution can be added dropwise to water and vigorously stirred causing precipitation of a poly(methacrylic acid)-block-poly(butylmethacrylate)-block-poly(methacrylic acid)-XDC. The precipitate can be collected using a vacuum funnel and vacuum-dried followed by hydrolysis in the presence of a strong base to remove XDC. As a result of the described process, an ABA block copolymer, poly(methacrylic acid)-block-poly(butyl methacrylate)-block-poly(methacrylic acid), can be precipitated, the ABA block copolymer having the general formula (VIII):

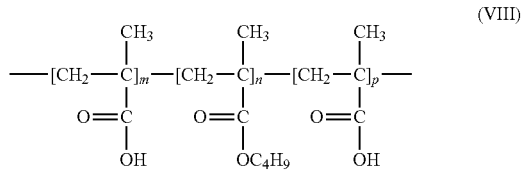

The molecular weight of the BMA-based mid-blocks (B blocks) in block-copolymer (VIII) can be about 85,000 Daltons as measured by GPC corresponding to the value of n ~

599, and the molecular weight of the methacrylic acid-based end blocks (A blocks) can be about 10,020 Daltons, corresponding to values of m ~116 and p ~116, resulting in molar ratio between units derived from MAA and BMA of about 14:72:14.

EXAMPLE 3

Synthesis of an ABA Block Copolymer #3 (PEG-acrylate-PBMA-PEG-acrylate)

As a first step, PBMA-XDC was synthesized as described in Example 1. As a second step, PBMA-XDC was combined in a vial with acryloyl poly(ethylene glycol) (acryloyl-PEG) and 2-butanone in the amounts shown in Table 6.

TABLE 6

| No. | Component | Theoretical amount of the component | | Experimental amount of the component | |
|---|---|---|---|---|---|
| | | mmol | g | mmol | g |
| 1 | PBMA-XDC | 0.0064 | 1.00 | 0.0059 | 0.93 |
| 2 | 2-butanone | — | 12.40 | — | 10.08 |
| 3 | Acryloyl-PEG | 0.625 | 0.25 | 0.778 | 0.29176 |

Acryloyl-PEG is a product of esterification of acrylic acid by PEG and has a formula (IX):

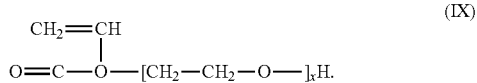

A low molecular weight acryloyl-PEG oligomer with the number-averaged molecular weight ($M_n$) of about 375 was used, corresponding to the value "x" in formula of (X) of about 7. The blend of PBMA-XDC, acryloyl-PEG and 2-butanone was subjected to UV radiation as described in Example 2, for about 43 hours. The vial was then opened, the contents were added dropwise to water and vigorously stirred at a temperature of about 70° C. for about 2 hours, causing evaporation of 2-butanone and forming a suspension of poly(acryloyl-PEG-block-butylmethacrylate-block-acryloyl-PEG)-XDC. The suspension was cooled to the room temperature and the precipitate was collected using a vacuum funnel and vacuum-dried followed by hydrolysis in the presence of a strong base to remove XDC. As a result of the described process, an ABA block copolymer, poly(acryloyl-PEG)-block-poly(butylmethacrylate)-block-poly(acryloyl-PEG), was precipitated, the ABA block copolymer having the general formula (X):

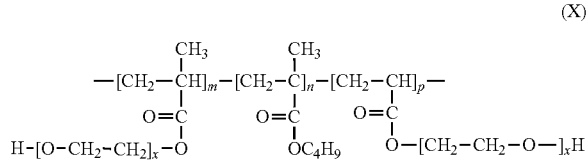

EXAMPLE 4

Synthesis of an ABA Block Copolymer #4 (PHEMA-PBMA-PHEMA)

As a first step, PBMA-XDC was synthesized as described in Example 1. As a second step, PBMA-XDC was combined in a vial with 2-hydroxyethyl methacrylate (HEMA) and 2-butanone in the amounts shown in Table 7.

TABLE 7

| No. | Component | Theoretical amount of the component | | Experimental amount of the component | |
|---|---|---|---|---|---|
| | | mmol | g | mmol | g |
| 1 | PBMA-XDC | 0.016 | 2.50 | 0.013 | 2.03 |
| 2 | 2-butanone | — | 12.40 | — | 10.19 |
| 3 | HEMA | 3.85 | 0.50 | 3.13 | 0.406 |

The blend of PBMA-XDC, HEMA and 2-butanone was subjected to UV radiation at a wavelength within a range of between about 310 nm and about 400 nm, for about 5 hours at room temperature (about 25° C.). The vial was then opened, about 1 ml of 1M solution of tert-butoxide in tetrahydrofuran was added, and the solvent was removed by evaporation. The contents of the vial were then dissolved in 100 ml of a blend of dimethylacetamide and water. The mass ratio between dimethylacetamide and water in the blend was about 1:1. The solution was then dialyzed against water for about 48 hours, and then dialyzed against methanol for about 24 hours. As a result of the described process, an ABA block copolymer, poly(2-hydroxyethyl methacrylate)-block-poly(butylmethacrylate)-block-poly(2-hydroxyethyl methacrylate), was precipitated, the ABA block copolymer having the general formula (XI):

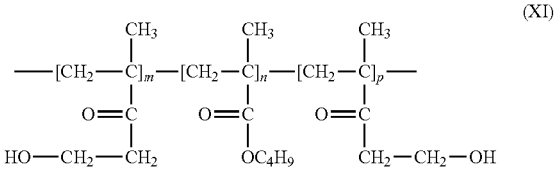

The molecular weight of the PBMA-based mid-blocks (B blocks) in block-copolymer (XI) was about 85,000 Daltons as measured by GPC corresponding to the value of n ~599, and the molecular weight of the poly(2-hydroxyethyl methacrylate)-based end blocks (A blocks) was about 10,020 Daltons, corresponding to values of m ~77 and p ~77. The weight ratio between the A blocks and the B blocks was about 10:80:10. Alternatively, if desired, the block copolymer can have the weight ratio between the A blocks and the B blocks of about 5:90:5. To obtain such polymer, those having ordinary skill in the art will choose an appropriate ratio between PBMA-XDC and HEMA in step 2 of the synthesis described above in this example.

EXAMPLE 5

Synthesis of an AB Block Copolymer (PSPMA-PBMA)

As a first step, a monomer BMA was dissolved in 2-butanone and an initiator BDC was added. The amounts of components are summarized in Table 8.

TABLE 8

| No. | Component | Amount of the component mmol | g |
|---|---|---|---|
| 1 | BMA | 140.8 | 20.0 |
| 2 | 2-butanone | — | 60.0 |
| 3 | BDC | 0.1 | 0.0239 |

The solution of BMA and BDC in 2-butanone was placed into a borosilicate vial, purged with dry nitrogen for about 30 minutes and the vial was sealed. The contents of vial were subjected to UV radiation at a wavelength within a range of between about 310 nm and about 400 nm, for about 12 hours. The vial was then opened and the contents were added, in a dropwise manner, to ethanol that was cooled to a temperature of about −76° C. As a result, poly(butylmethacrylate)-BDC (PBMA-BDC) was precipitated. The molecular weight of the PBMA-BDC was about 200,000 Daltons as measured by GPC. The precipitate was collected using a vacuum funnel and vacuum-dried.

As a second step, PBMA-BDC obtained as described above was combined with 3-sulfopropylmethacrylate and a 2% (mass) solution of PEG having weight average molecular weight of about 750 in aqueous 2-butanone. The amounts of components are shown in Table 9.

TABLE 9

| No. | Component | Weight fraction | Amount, grams |
|---|---|---|---|
| 1 | PBMA-BDC | 0.75 | 15.00 |
| 2 | 3-sulfopropylmethacrylate | 0.25 | 5.00 |
| 3 | 2% PEG in 2-butanone/water | — | 60.00 |

The blend of PBMA-BDC, 3-sulfopropylmethacrylate, and the PEG solution in aqueous 2-butanone was placed into a borosilicate vial, purged with dry nitrogen for about 10 minutes and the vial was sealed. The contents of vial were subjected to UV radiation at a wavelength within a range of between about 310 nm and about 400 nm, for about 12 hours. The vial was then opened and the contents were added dropwise to water and vigorously stirred causing precipitation of a poly(3-sulfopropylmethacrylate)-block-poly(butylmethacrylate)-BDC, having molecular weight of about 266,700 Daltons. The precipitate was collected using a vacuum funnel and vacuum-dried followed by hydrolysis in the presence of a strong base to remove BDC. As a result of the described process, an AB block copolymer, poly(3-sulfopropylmethacrylate)-block-poly(butylmethacrylate), was precipitated, the AB block copolymer having the general formula (XII):

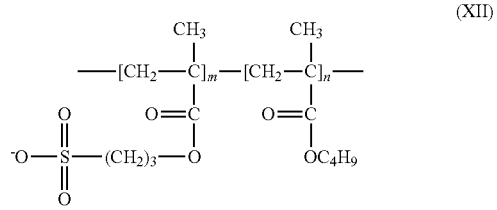

(XII)

The molecular weight of the PBMA-based blocks (B blocks) was about 200,000 Daltons as measured by GPC corresponding to the value of n ~1,400, the molecular weight of the poly(3-sulfopropylmethacrylate)-based blocks (A blocks) was about 66,700 Daltons, corresponding to values of m ~324. Overall molecular weight of the block copolymer was about 266,700 Daltons.

EXAMPLE 6

Synthesis of a Random Copolymer #1 P (BMA-HEMA)

A solution was prepared by thoroughly mixing the following components:
(a) about 48.02 mass % BMA;
(b) about 5.33 mass % HEMA;
(c) about 1.60 mass % of initiator 2,2-dimethoxy-2-phenol acetophenone; and
(f) the balance, benzene.

An inert atmosphere was created by bubbling nitrogen gas through the solution for about 30 minutes. The solution was then be exposed to UV radiation for about 10 minutes at a wavelength of 360 nm while being continuously stirred causing formation of a random copolymer, poly(butyl methacrylate-co-2-hydroxyethyl methacrylate), P(BMA-HEMA).

The final P(BMA-HEMA) random copolymer was precipitated with a non-solvent such as hexane and vacuum dried. The copolymer had a mass ratio between the units derived from BMA and the units derived from HEMA of about 90:10. Alternatively, if desired, the copolymer can have the mass ratio between the units derived from BMA and the units derived from HEMA of about 80:20. To obtain such copolymer, those having ordinary skill in the art will choose an appropriate ratio between BMA and HEMA in the synthesis described above in this Example.

EXAMPLE 7

Synthesis of a Random Copolymer #2 P(MMA-BMA-AA-PEGA)

A solution can be prepared by thoroughly mixing the following components:
(a) about 15 mass % MMA;
(b) about 9 mass % BMA;
(c) about 8 mass % PEG-acrylate (PEGA), where PEG can have weight-average molecular weight of about 6,000;
(d) about 20 mass % acrylic acid (AA);
(e) about 3 mass % initiator 2,2-dimethoxy-2-phenol acetophenone; and
(f) the balance, benzene.

An inert atmosphere can be created by bubbling nitrogen gas through the solution for about 30 minutes. The solution can then be exposed to UV radiation for about 10 minutes at a wavelength of 360 nm while being continuously stirred causing formation of a random copolymer, P(MMA-BMA-AA-PEGA).

The final P(MMA-BMA-AA-PEGA) random copolymer can be precipitated with a non-solvent such as hexane and vacuum dried. The copolymer can then be mixed with EVAL in a mass ratio of about 2:3 and the mixture can be applied onto a stent to form a reservoir layer or a topcoat layer.

EXAMPLE 8

A first composition was prepared by mixing the following components:
(a) about 2.0 mass % BIOSPAN polymer; and
(b) the balance, a solvent blend containing dimethylacetamide (DMAC) and pentane, the mass ratio between DMAC and pentane in the blend was about 4:1.

The first composition was applied onto the surface of a bare 13 mm TETRA stent (available from Guidant Corporation) by spraying and dried to form a primer layer. A spray coater was used having a 0.014 fan nozzle maintained at about 60° C. with a feed pressure of about 0.2 atm (about 3 psi) and an atomization pressure of about 1.3 atm (about 20 psi). The primer was baked at about 80° C. for about 1 hour, yielding a dry primer layer. The dry primer layer contained about 100 µg of BIOSPAN polymer.

A second composition was prepared by mixing the following components:
  (a) about 1.8 mass % BIOSPAN polymer;
  (b) about 0.2 mass % c-RGD; and
  (c) the balance, a solvent blend containing DMAC and pentane, the mass ratio between DMAC and pentane in the blend was about 4:1.

The mass ratio between c-RGD and the BIOSPAN polymer in the second composition was about 1:9. Overall, the second composition contained the total of about 600 µg of the BIOSPAN/c-RGD mixture. The second composition was applied onto the dried primer layer to form the reservoir layer, using the same spraying technique and equipment used for applying the primer layer, followed by drying, i.e., by baking at about 50° C. for about 2 hours, yielding a dry reservoir layer.

EXAMPLE 9

A first composition was prepared by mixing the following components:
  (a) about 2.0 mass % PBMA; and
  (b) the balance, a solvent blend of acetone and cyclohexanone in a mass ratio of about 7:3.

The first composition was applied onto the surface of a bare 13 mm TETRA stent, using technique described in Example 8. The primer was baked at about 80° C. for about 30 minutes, yielding a dry primer layer. The dry primer layer contained about 60 µg of PBMA.

A second composition was prepared by mixing the following components:
  (a) about 1.8 mass % BIOSPAN polymer;
  (b) between about 0.2 mass % c-RGD; and
  (c) the balance, a solvent blend containing DMAC and pentane, the mass ratio between DMAC and pentane in the blend was about 4:1.

The mass ratio between c-RGD and the BIOSPAN polymer in the second composition was about 1:9. Overall, the second composition contained the total of about 500 µg of the BIOSPAN/c-RGD mixture. The second composition was applied onto the dried primer layer to form the reservoir layer, using the same spraying technique and equipment used for applying the primer layer, followed by drying, i.e., by baking at about 80° C. for about 30 minutes, yielding a dry reservoir layer.

A third composition was prepared by mixing the following components:
  (a) about 2.0 mass % SOLEF 21508 ("SOLEF") polymer; and
  (b) the balance, a solvent blend of acetone and cyclohexanone in a mass ratio of about 7:3.

SOLEF 21508 is a trade name of poly(vinylidene fluoride-co-hexafluoropropene) available from Solvay Fluoropolymers, Inc. of Houston, Tex. The third composition was applied onto the dried reservoir layer to form a topcoat layer, using the same spraying technique and equipment used for applying the primer layer and the reservoir layer. The wet topcoat layer was dried and baked at about 50° C. for about 2 hours, yielding a dry topcoat layer. The dry topcoat layer contained about 200 µg of the SOLEF polymer.

The coated stent was subjected to an in vitro mechanical test according to the following procedure. The stent was guided through a tortuous path and then deployed in a poly(vinyl alcohol) (PVA) lesion having approximate size of about 3 by 10 millimeters. The tortuous path and the lesion contained de-ionized water at about 37° C. To deploy the stent, pressure of about 12 atm was applied to the balloon for about 1 minute, followed by deflating of the balloon and retraction of the catheter. After the catheter was retracted, de-ionized water was pumped through the tortuous path and the lesion for about 1 hour at a rate of about 50 milliliters per minute. Water was maintained at about 37° C.

Overall views of the coated stent which underwent the simulated in-vitro testing are shown by the microphotographs on FIGS. 1A-1F. After the simulated use test, the quality of the stent coatings was good. No substantial porosity of the coating on the outer surface areas was observed. The damage of the coatings was only minimal, and the mechanical integrity of the coating was preserved.

EXAMPLE 10

Figure 2:
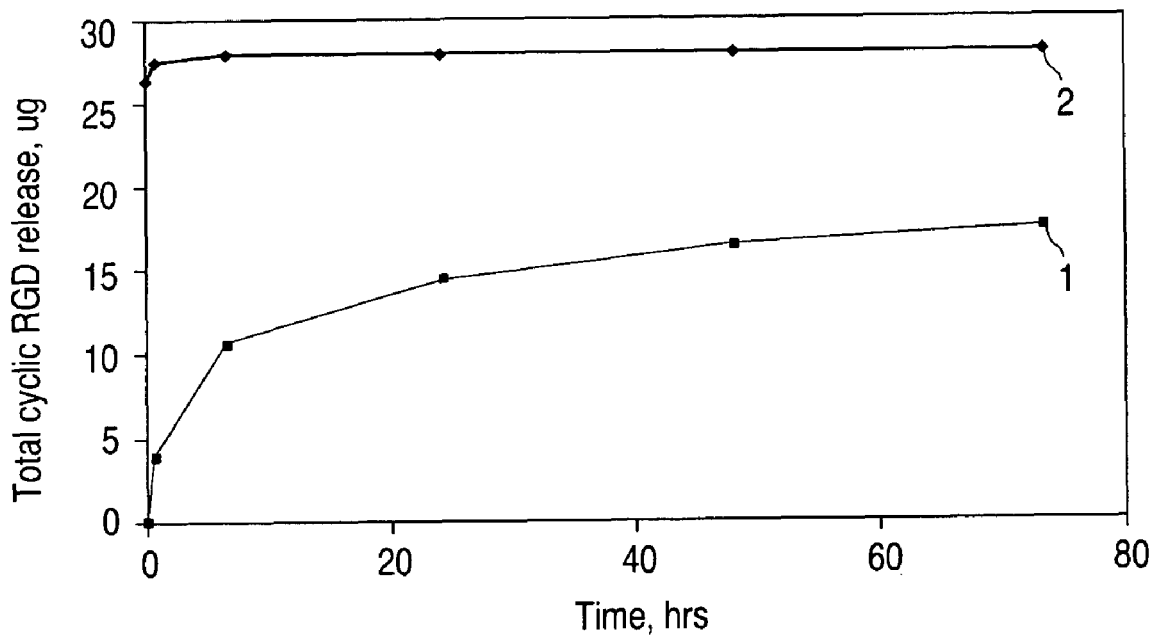
FIGS. 2, 3, and 6 are graphs illustrating the rate of release of a drug from stents coated according to embodiments of the present invention.

The stent was coated as in Example 9, except the mass ratio between c-RGD and the BIOSPAN polymer in the second composition was about 1:6. Following the fabrication of the stent coating, the rate of release of c-RGD from the stent was determined. The coated stent was immersed in an aqueous phosphate buffered saline solution, the solution was maintained at a temperature of about 37° C., and the drug release was periodically measured by the high pressure liquid chromatography (HPLC) method, while the temperature of the solution was maintained constant at about 37° C. As shown by the graph presented by FIG. 2, the rate of release for the stent having a SOLEF topcoat (curve 1) is substantially reduced compared to the stent coating having no topcoat (curve 2).

EXAMPLE 11

A primer was formed on a 13 mm TETRA stent as described in Example 9. A composition was prepared by mixing the following components:
  (a) about 1.8 mass % BIOSPAN polymer;
  (b) about 0.2 mass % c-RGD; and
  (c) the balance, a solvent blend containing DMAC and pentane, the mass ratio between DMAC and pentane in the blend was about 4:1.

The mass ratio between c-RGD and the BIOSPAN polymer in the first composition was about 1:9. Overall, the second composition contained the total of about 500 µg of the BIOSPAN/c-RGD mixture. The composition was applied onto the dried primer layer to form the reservoir layer, using the same spraying technique and equipment used for applying the primer layer, followed by drying, i.e., by baking at about 80° C. for about 30 minutes, yielding a dry reservoir layer.

Following the formation of the dry reservoir layer, a SOLEF-based topcoat layer was formed over the reservoir layer as described in Example 9. The stent coating was tested in vitro as described in Example 9, and likewise showed good mechanical qualities while providing a sustained release of c-RGD.

EXAMPLE 12

A primer was formed on a 13 mm TETRA stent as described in Example 9. A first composition was prepared by mixing the following components:

(a) about 1.5 mass % PHEMA-PBMA-PHEMA ABA block-copolymer synthesized as described in Example 4, the block copolymer containing about 90 mass % of PBMA blocks and about 5 mass % of each of the PHEMA blocks;

(b) about 0.5 mass % c-RGD; and (c) the balance, a solvent blend of dimethylacetamide and methanol in a mass ratio of about 7:3.

The mass ratio between c-RGD and the ABA block-polymer in the first composition was about 1:3. Overall, the first composition contained the total of about 440 μg of the ABA block-copolymer/c-RGD mixture, which means that about 110 μg of c-RGD was deposited onto the stent. The first composition was applied onto the dried primer layer to form the reservoir layer, using the same spraying technique and equipment used for applying the primer layer, followed by drying, i.e., by baking at about 80° C. for about 30 minutes, yielding a dry reservoir layer.

A second composition was prepared by mixing the following components:

(a) about 2.0 mass % PBMA; and (b) the balance, a solvent blend of acetone and cyclohexanone in a mass ratio of about 7:3.

The second composition was applied onto the dried reservoir layer to form a topcoat layer, using the same spraying technique and equipment used for applying the primer layer and the reservoir layer. The wet topcoat layer was dried and baked at about 80° C. for about 30 minutes, yielding a dry topcoat layer. The dry topcoat layer contained about 200 μg of PBMA.

EXAMPLE 13

A primer was formed on a 13 mm TETRA stent as described in Example 9. A composition was prepared by mixing the following components:

(a) about 1.8 mass % PHEMA-PBMA-PHEMA block-copolymer synthesized as described in Example 4, the block copolymer containing about 90 mass % of PBMA blocks and about 5 mass % of each of the PHEMA blocks;

(b) about 0.2 mass % c-RGD; and (c) the balance solvent blend of dimethylacetamide and methanol in a mass ratio of about 7:3.

The mass ratio between c-RGD and the block-polymer in the first composition was about 1:9. Overall, the composition contained the total of about 500 μg of the block-copolymer/c-RGD mixture, which means that about 40 μg of c-RGD was deposited onto the stent.

The composition was applied onto the dried primer layer to form the reservoir layer, using the same spraying technique and equipment used for applying the primer layer, followed by drying, i.e., by baking at about 80° C. for about 30 minutes, yielding a dry reservoir layer.

EXAMPLE 14

A 13 mm TETRA stent was coated as described in Example 13. A composition was prepared by mixing the following components:

(a) about 2.0 mass % SOLEF polymer; and (b) the balance, a solvent blend containing acetone and cyclohexanone, the mass ratio between acetone and pentane in the blend was about 7:3.

The composition was applied onto the dried reservoir layer to form a topcoat layer.

EXAMPLE 15

Figure 3:
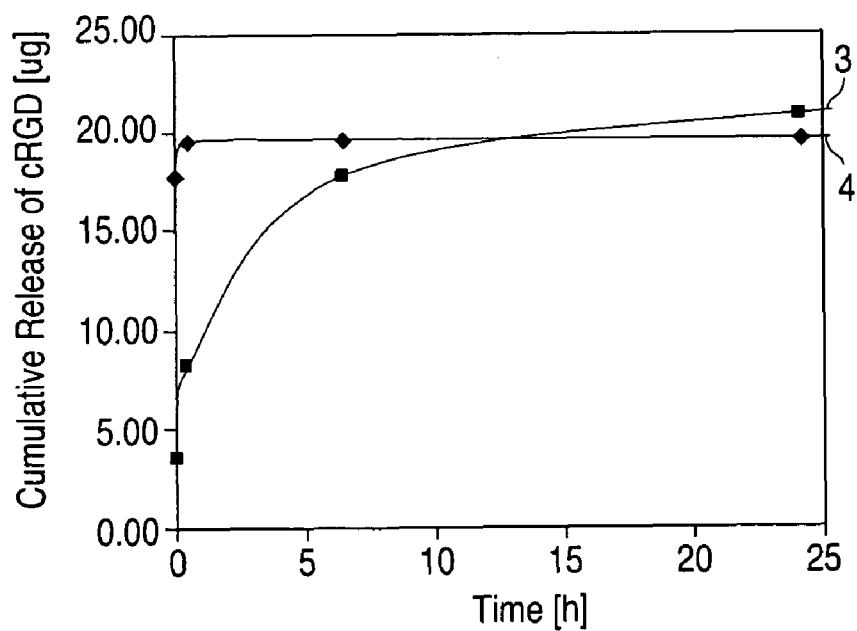

The rate of release of c-RGD from the stents coated as described in Examples 13 and 14 was determined using the HPLC technique as described in Example 9. The results are shown by FIG. 3. As can be seen from the results presented by FIG. 3, the rate of release for the stent having a SOLEF topcoat (curve 3) is substantially reduced compared to the stent coating having no topcoat (curve 4), especially in the initial stages of the release. Clearly, the stent coating having no topcoat does not control the release of c-RGD.

EXAMPLE 16

A first composition was prepared by mixing the following components:

(a) about 2.0 mass % PBMA; and (b) the balance, a solvent blend of acetone and cyclohexanone in a mass ratio of about 7:3.

The first composition was applied onto the surface of a bare 12 mm VISION stent (available from Guidant Corp.), using technique described in Example 8. The primer was baked at about 80° C. for about 30 minutes, yielding a dry primer layer. The dry primer layer contained about 100 μg of PBMA.

A second composition was prepared by mixing the following components:

(a) about 1.8 mass % BIOSPAN polymer;

(b) between about 0.2 mass % c-RGD; and (c) the balance, a solvent blend containing DMAC and pentane, the mass ratio between DMAC and pentane in the blend was about 4:1.

The mass ratio between c-RGD and the BIOSPAN polymer in the second composition was about 1:9. Overall, the second composition contained the total of about 500 μg of the BIOSPAN/c-RGD mixture. The second composition was applied onto the dried primer layer to form the reservoir layer, using the same spraying technique and equipment used for applying the primer layer, followed by drying, i.e., by baking at about 80° C. for about 30 minutes, yielding a dry reservoir layer.

A third composition was prepared by mixing the following components:

(a) about 2.0 mass % SOLEF polymer; and (b) the balance, a solvent blend containing acetone and cyclohexanone, the mass ratio between acetone and cyclohexanone in the blend was about 7:3.

The third composition was applied onto the dried reservoir layer to form a topcoat layer, using the same spraying technique and equipment used for applying the primer layer and the reservoir layer. The wet topcoat layer was dried and baked at about 80° C. for about 30 minutes, yielding a dry topcoat layer. The dry topcoat layer contained about 200 μg of the SOLEF polymer.

Figure 4:

The coated stent was subjected to an in vitro mechanical test according to the procedure described in Example 9. Overall view of the coated stent which underwent the simulated in vitro testing is shown by the microphotograph of FIG. 4. After the simulated use test, the quality of the stent coating was good. No substantial porosity of the coating on the outer surface areas was observed. The damage of the coatings was only minimal, and the mechanical integrity of the coating was preserved.

EXAMPLE 17

A first composition was prepared by mixing the following components:

(a) about 2.0 mass % PBMA; and (b) the balance, a solvent blend of acetone and cyclohexanone in a mass ratio of about 7:3.

The first composition was applied onto the surface of a bare 12 mm VISION stent, using technique described in Example 8. The primer was baked at about 80° C. for about 30 minutes, yielding a dry primer layer. The dry primer layer contained about 100 μg of PBMA.

A second composition was prepared by mixing the following components:

(a) about 1.714 mass % PHEMA-PBMA-PHEMA ABA block-copolymer synthesized as described in Example 4, the block copolymer containing about 90 mass % of PBMA blocks and about 5 mass % of each of the PHEMA blocks;

(b) about 0.286 mass % c-RGD; and (c) the balance, a solvent blend of dimethylacetamide and methanol in a mass ratio of about 7:3.

The mass ratio between c-RGD and the ABA block-polymer in the second composition was about 1:6. Overall, the second composition contained the total of about 500 μg of the ABA block-copolymer/c-RGD mixture. The second composition was applied onto the dried primer layer to form the reservoir layer, using the same spraying technique and equipment used for applying the primer layer, followed by drying, i.e., by baking at about 80° C. for about 30 minutes, yielding a dry reservoir layer.

A third composition was prepared by mixing the following components:

(a) about 2.0 mass % SOLEF polymer; and (b) the balance, a solvent blend of acetone and cyclohexanone in a mass ratio of about 7:3.

The third composition was applied onto the dried reservoir layer to form a topcoat layer, using the same spraying technique and equipment used for applying the primer layer and the reservoir layer. The wet topcoat layer was dried and baked at about 80° C. for about 30 minutes, yielding a dry topcoat layer. The dry topcoat layer contained about 200 μg of the SOLEF polymer.

Figure 5:

The coated stent was subjected to an in-vitro mechanical test according to the procedure described in Example 9. Overall view of the coated stent which underwent the simulated in-vitro testing is shown by the microphotograph on FIG. 5. After the simulated use test, the quality of the stent coating was acceptable.

Figure 6:
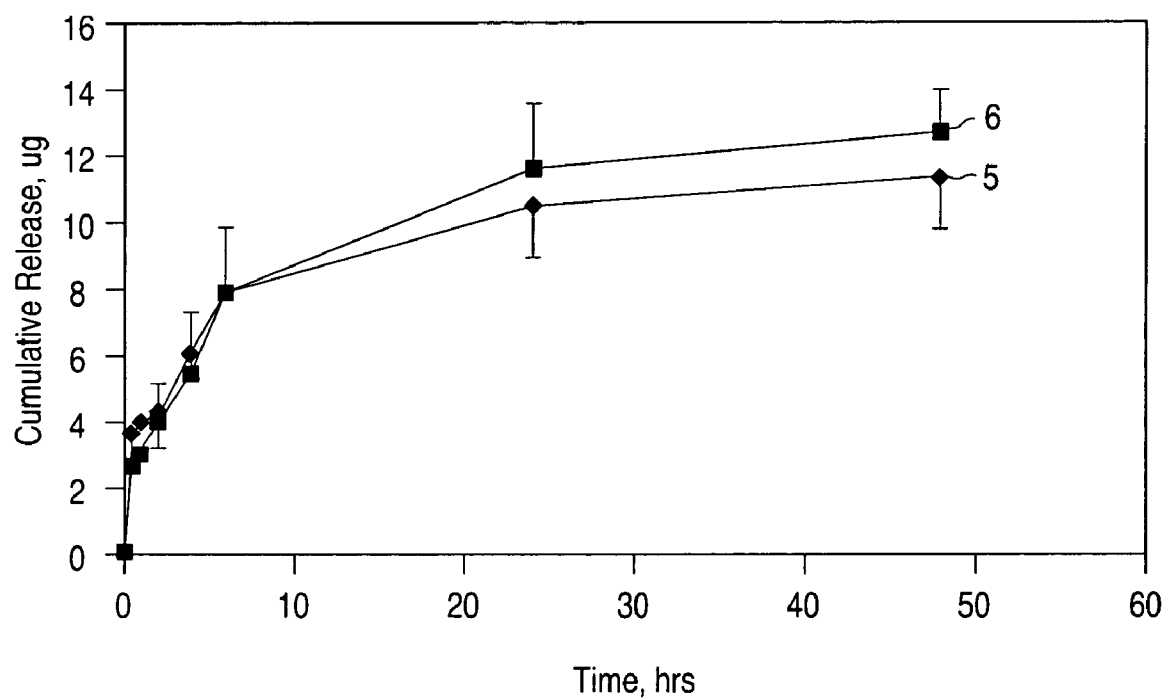

The rate of release of c-RGD from the stent coated as described above was also determined using the HPLC technique described in Example 9. Two separate stents coated as described above were tested. One test was expanded and another was not expanded. As shown by the graph presented by FIG. 6, the rate of release for the stent having a SOLEF topcoat was satisfactory, for the stent coating on both the expanded stent (curve 5) and the unexpanded stent (curve 6).

The compositions of the coatings described in Examples 8-14, 16, and 17 are summarized in Table 10.

TABLE 10

| Example | Stent Type | Primer | Reservoir Composition (1) P[*] (2) D[*] | D:P Ratio[*] | Topcoat |
|---|---|---|---|---|---|
| 8 | 13 mm TETRA | BIOSPAN | (1) BIOSPAN (2) c-RGD | 1:9 | None |
| 9 | 13 mm TETRA | PBMA | (1) BIOSPAN (2) c-RGD | 1:9 | SOLEF |
| 10 | 13 mm TETRA | PBMA | (1) BIOSPAN (2) c-RGD | 1:6 | SOLEF |
| 11 | 13 mm TETRA | PBMA | (1) BIOSPAN (2) c-RGD | 1:9 | SOLEF |
| 12 | 13 mm TETRA | PBMA | (1) PHEMA-PBMA-PHEMA (2) c-RGD | 1:3 | PBMA |
| 13 | 13 mm TETRA | PBMA | (1) PHEMA-PBMA-PHEMA (2) c-RGD | 1:9 | None |
| 14 | 13 mm TETRA | PBMA | (1) PHEMA-PBMA-PHEMA (2) c-RGD | 1:9 | SOLEF |
| 16 | 12 mm VISION | PBMA | (1) BIOSPAN (2) c-RGD | 1:9 | SOLEF |
| 17 | 12 mm VISION | PBMA | (1) PHEMA-PBMA-PHEMA (2) c-RGD | 1:6 | SOLEF |

[*]D = Drug;
P = Polymer

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A medical article, comprising an implantable substrate and a coating disposed at least on a portion of the substrate, the coating including an amphiphilic copolymer comprising at least one hydrophobic moiety and at least one hydrophilic moiety,
    wherein at least one hydrophilic moiety comprises 2-acrylamido-2-methyl-1-propanesulfonic acid, 3-sulfopropyl acrylate, 3-sulfopropyl methacrylate, or 3-allyloxy-2-hydroxypropanesulfonic acid, and
    wherein the coating includes a therapeutic agent incorporated or dispersed in the coating in a mass ratio of the therapeutic agent to the amphiphilic copolymer between about 1:10 and about 1:3.

2. The medical article of claim 1, wherein the amphiphilic copolymer comprises an acrylic copolymer.

3. The medical article of claim 2, wherein the acrylic copolymer is a block copolymer or a random copolymer.

4. The medical article of claim 3, wherein the block copolymer is an ABA block copolymer or an AB block-copolymer.

5. The medical article of claim 1, wherein the hydrophobic moiety is selected from a group consisting of methyl methacrylate, ethyl methacrylate, n-butyl methacrylate, and lauryl methacrylate.

6. The medical article of claim 1, wherein the amphiphilic copolymer is a product of living free radical copolymerization of plurality of monomers with initiation-transfer agent termination of the living macro-chains.

7. The medical article of claim 1, wherein the therapeutic agent is selected from a group consisting of cyclic-RGD peptide, poly(L-arginine), poly(D-arginine), poly(D,L-arginine), poly(L-lysine), poly(D-lysine), poly(δ-guanidino-α-aminobutyric acid), a racemic mixture of poly(L-arginine) with poly(D-arginine), elastin mimetic polypeptides, and blends thereof.

8. The medical article of claim 1, wherein the coating comprises a small-molecule water soluble drug.

9. A medical article, comprising an implantable substrate and a coating disposed at least on a portion of the substrate, the coating including an amphiphilic copolymer comprising at least one hydrophobic moiety and at least one hydrophilic moiety, wherein the amphiphilic copolymer has a formula

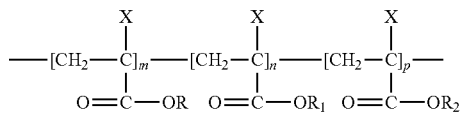

wherein
(a) each of m, n, and p is, independently, an integer, wherein m >0, n >0, and p >0;
(b) X, Y, and Z each is independently hydrogen or an alkyl group; and
(c) R, $R_1$, $R_2$ is independently a straight-chained or branched substituted or unsubstituted alkyl group, or substituted or unsubstituted aryl group, wherein at least one of R and $R_2$ is 3-sulfopropyl;
wherein the coating further includes a therapeutic agent incorporated or dispersed in the coating.

10. The medical article of claim 9, wherein the block copolymer is an ABA block copolymer or an AB block-copolymer.

11. The medical article of claim 9, wherein the amphiphilic copolymer comprises PSPMA-PBMA-PSPMA, or PSPMA-PBMA, wherein PSPMA is poly 3-sulfopropyl methacrylate, PBMA is poly(butylmethacrylate).

12. The medical article of claim 9, wherein the therapeutic agent is selected from a group consisting of cyclic-RGD peptide, poly(L-arginine), poly(D-arginine), poly(D,L-arginine), poly(L-lysine), poly(D-lysine), poly(δ-guanidino-α-aminobutyric acid), a racemic mixture of poly(L-arginine) with poly(D-arginine), elastin mimetic polypeptides, and blends thereof.

* * * * *